United States Patent
Liu et al.

(10) Patent No.: US 12,343,111 B2
(45) Date of Patent: Jul. 1, 2025

(54) METHODS AND SYSTEMS FOR MRI PATIENT PRESCREENING

(71) Applicant: GE Precision Healthcare LLC, Milwaukee, WI (US)

(72) Inventors: Yuechen Liu, Beijing (CN); Fan Yang, Beijing (CN); Kun Wang, Beijing (CN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 673 days.

(21) Appl. No.: 16/563,769

(22) Filed: Sep. 6, 2019

(65) Prior Publication Data

US 2021/0068699 A1 Mar. 11, 2021

(51) Int. Cl.
 A61B 5/00 (2006.01)
 G01R 33/28 (2006.01)
 G01R 33/341 (2006.01)
 G01R 33/54 (2006.01)

(52) U.S. Cl.
 CPC .......... *A61B 5/0037* (2013.01); *G01R 33/285* (2013.01); *G01R 33/288* (2013.01); *G01R 33/341* (2013.01); *G01R 33/546* (2013.01)

(58) Field of Classification Search
 CPC ..... A61B 5/0037; A61B 5/015; A61B 5/0507; A61B 5/053; A61B 5/055; A61B 5/061; A61B 5/062; A61B 5/063; A61B 5/4842; A61B 5/4851; A61B 5/746; A61B 8/0833; G01R 33/285; G01R 33/288; G01R 33/341; G01R 33/546
 See application file for complete search history.

(56) References Cited

U.S. PATENT DOCUMENTS

| | | | | |
|---|---|---|---|---|
| 7,528,603 | B2 * | 5/2009 | Hayakawa | G01R 33/28 324/318 |
| 2010/0137945 | A1 * | 6/2010 | Gadagkar | A61N 1/3718 607/60 |
| 2012/0105267 | A1 * | 5/2012 | DeLia | G06V 10/36 378/70 |
| 2014/0028457 | A1 * | 1/2014 | Reinpoldt | G06K 9/00771 340/552 |
| 2014/0257089 | A1 * | 9/2014 | Rapoport | A61B 5/062 600/424 |
| 2014/0328450 | A1 * | 11/2014 | Pal | G01N 23/046 378/20 |

(Continued)

FOREIGN PATENT DOCUMENTS

WO 2016206969 A1 12/2016

OTHER PUBLICATIONS

Shellock et al., "Detection of Implants and other Objects using Ferromagnetic Detection Systems: Implications for Patient Screening before MRI", ARJ Oct. 2013 (Year: 2013).*

(Continued)

*Primary Examiner* — Christopher L Cook
(74) *Attorney, Agent, or Firm* — McCoy Russell LLP

(57) ABSTRACT

Various methods and systems are provided for pre-screen procedure for medical imaging. In one example, a method for the pre-screen procedure includes receiving data from a scanning assembly positioned away from an MRI scanner, identifying the implant based on a matching of the implant to an implant database, and displaying identification of the implant.

20 Claims, 7 Drawing Sheets

(56) References Cited

U.S. PATENT DOCUMENTS

| | | | |
|---|---|---|---|
| 2014/0376336 A1* | 12/2014 | Steckner | G01R 33/288 |
| | | | 367/197 |
| 2014/0378820 A1 | 12/2014 | Gururaj et al. | |
| 2015/0253422 A1* | 9/2015 | Morton | G01S 13/0209 |
| | | | 324/642 |
| 2016/0252592 A1 | 9/2016 | Van Den Brink | |
| 2016/0283676 A1* | 9/2016 | Lyon | G16H 10/20 |
| 2016/0302692 A1* | 10/2016 | Demmer | A61B 5/6898 |
| 2017/0212913 A1* | 7/2017 | Kurse | G01R 33/288 |
| 2017/0311841 A1* | 11/2017 | Rothgang | A61B 5/74 |
| 2017/0337447 A1* | 11/2017 | Smith | G01V 5/0008 |
| 2018/0038923 A1* | 2/2018 | Van Meel | G01R 33/288 |
| 2018/0172785 A1* | 6/2018 | Leussler | G01R 33/341 |
| 2019/0231433 A1* | 8/2019 | Amanatullah | A61B 17/1703 |
| 2020/0249156 A1* | 8/2020 | Wu | G06N 20/00 |

OTHER PUBLICATIONS

Zhang et al., "Terahertz Image Detection with Improved Faster Region-Based Convolutional Neural Network", Sensors, Jul. 2018 (Year: 2018).*

* cited by examiner

METHODS AND SYSTEMS FOR MRI PATIENT PRESCREENING

FIELD

Embodiments of the subject matter disclosed herein relate to magnetic resonance imaging, and more particularly, to a pre-screen routine for magnetic resonance imaging of a patient.

BACKGROUND

Magnetic resonance imaging (MRI) is a non-ionizing medical imaging modality that can create images of the inside of a human body without using x-rays. A strong, uniform, static magnetic field $B_0$ is created by a superconducting magnet in MRI systems, the magnetic field $B_0$ causing nuclear spins associated with hydrogen nuclei in tissue water to become polarized. The magnetic moments associated with these spins become preferentially aligned along the direction of the magnetic field $B_0$, resulting in a small net tissue magnetization along that axis. By creating a signature resonance frequency at each location in the body via gradient coils producing orthogonal magnetic fields, hydrogen nuclei are excited by a radio frequency signal at or near the resonance frequency of the hydrogen nuclei. As the nuclear spins relax back to their rest energy state, they release the absorbed energy in the form of an RF signal which is detected by one or more RF coil elements and is transformed into the image using reconstruction algorithms. Presence of metallic objects, such as a medical implant, in the body may be problematic due to magnetization of the implant by the strong magnetic field $B_0$ generated by MRI systems. The magnetic field $B_0$ may cause shifting of the implant and/or disruption to implant operation.

Patients with implants may not be able to have a magnetic resonance (MR) scan or the implant may be found to be incompatible with MRI during the MR scan if not screened properly. Usually before an MR scan, a patient is pre-screened to determine whether the patient can have the MR scan. However, current pre-screen procedures may provide limited information or inaccurate information. In some instances, a radiologist may ignore the pre-screening, resulting in issues to patients with implants. This disclosure sets up a preparation workflow for every patient before he or she walks into the MR scan room. Radiologists can rely on the pre-screen to obtain implant-specific information to determine whether the patient can have an MR exam and can be informed of any additional actions to ensure a safe MR scan.

BRIEF DESCRIPTION

In one embodiment, a method for a pre-screen procedure for magnetic resonance imaging (MRI), comprises using a pre-screen system to obtain data comprising a body model of a subject and presence of an implant in the subject, identifying the implant based on a matching of the implant to an implant database, and displaying the implant relative to the body model and identification of the implant. In this way, a presence of an implant may be efficiently located and identified in a patient by utilizing a plurality of pre-screen operations.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
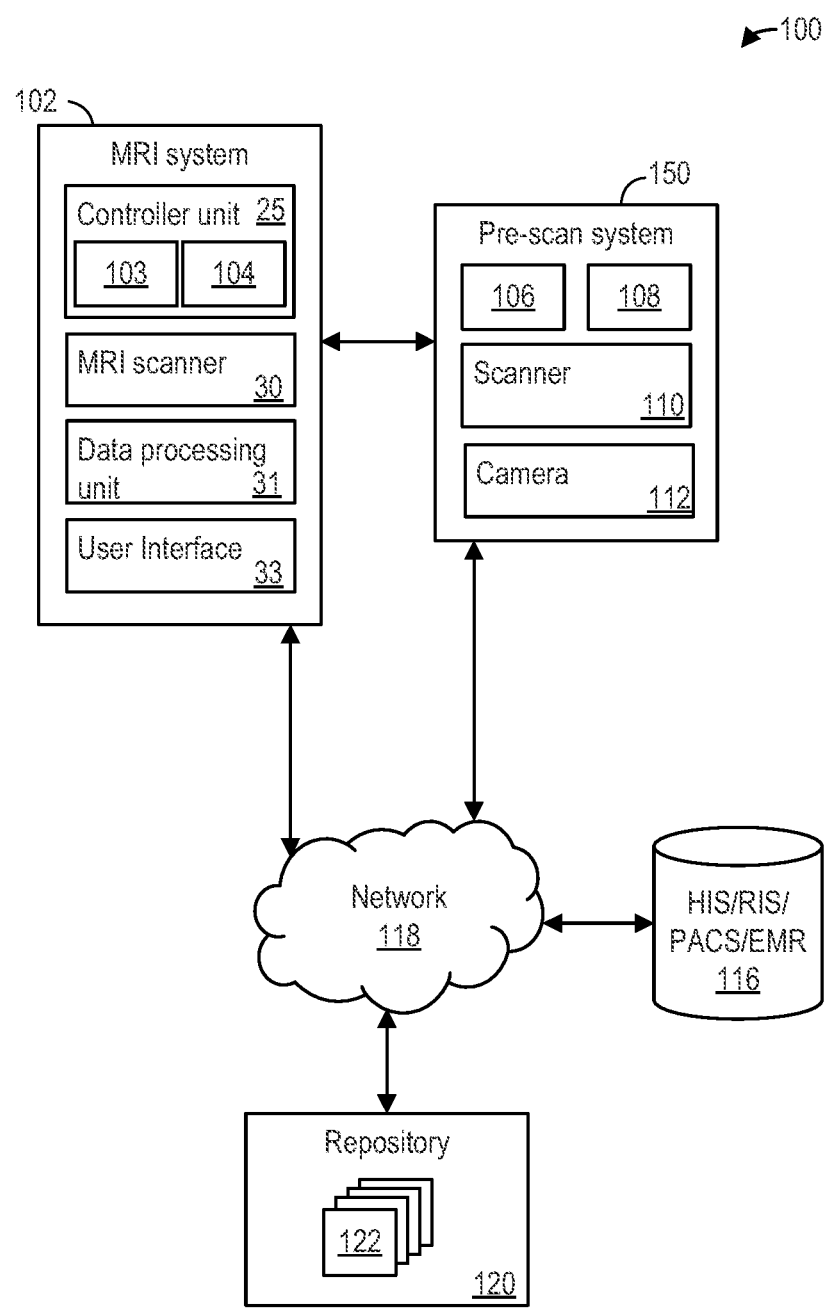
FIG. 1 shows a block schematic diagram of an architecture for MRI pre-screen according to an exemplary embodiment.
Figure 3:
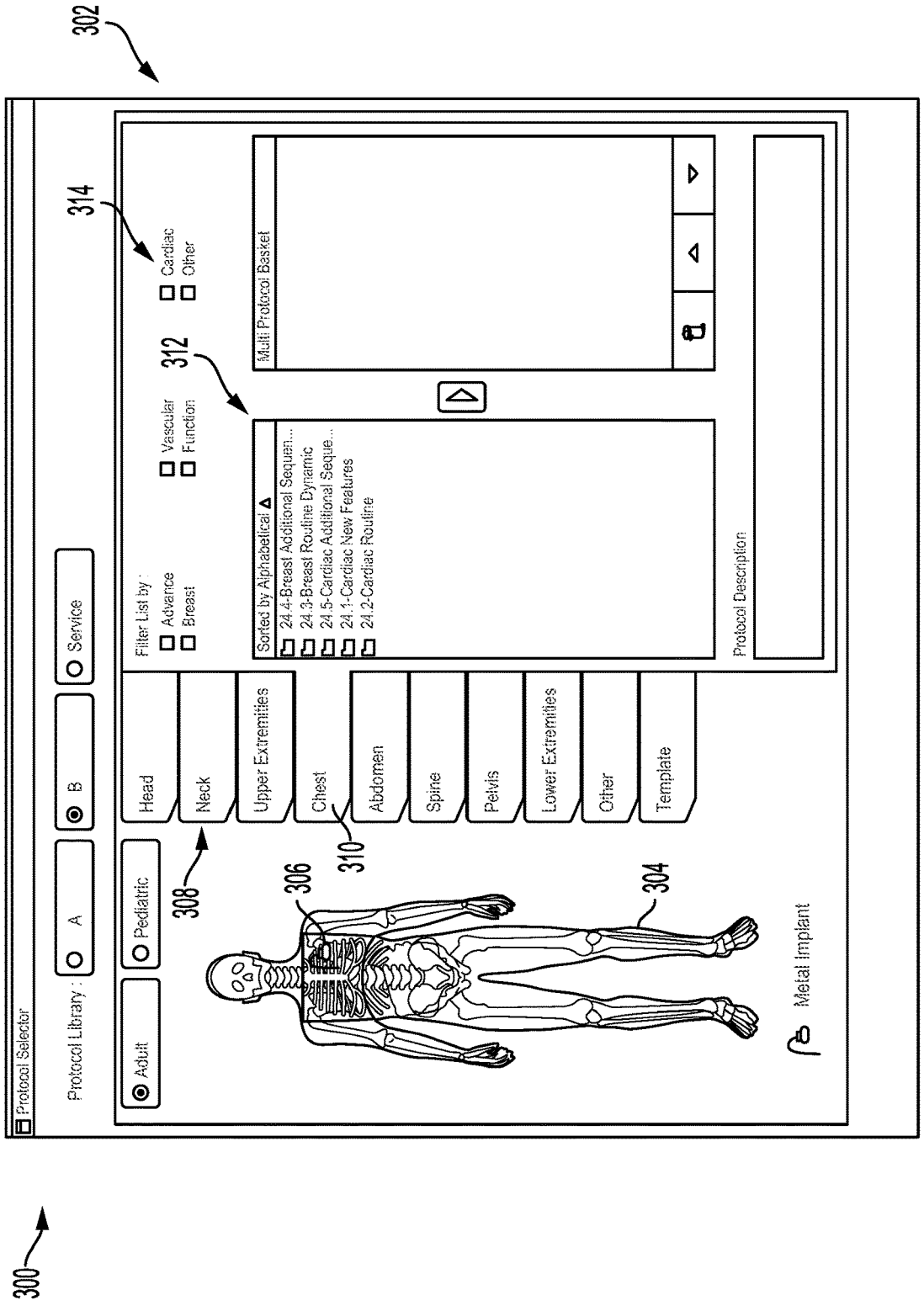
FIG. 3 shows a first image of a user interface illustrating location of an implant in a patient according to an exemplary embodiment.
Figure 4:
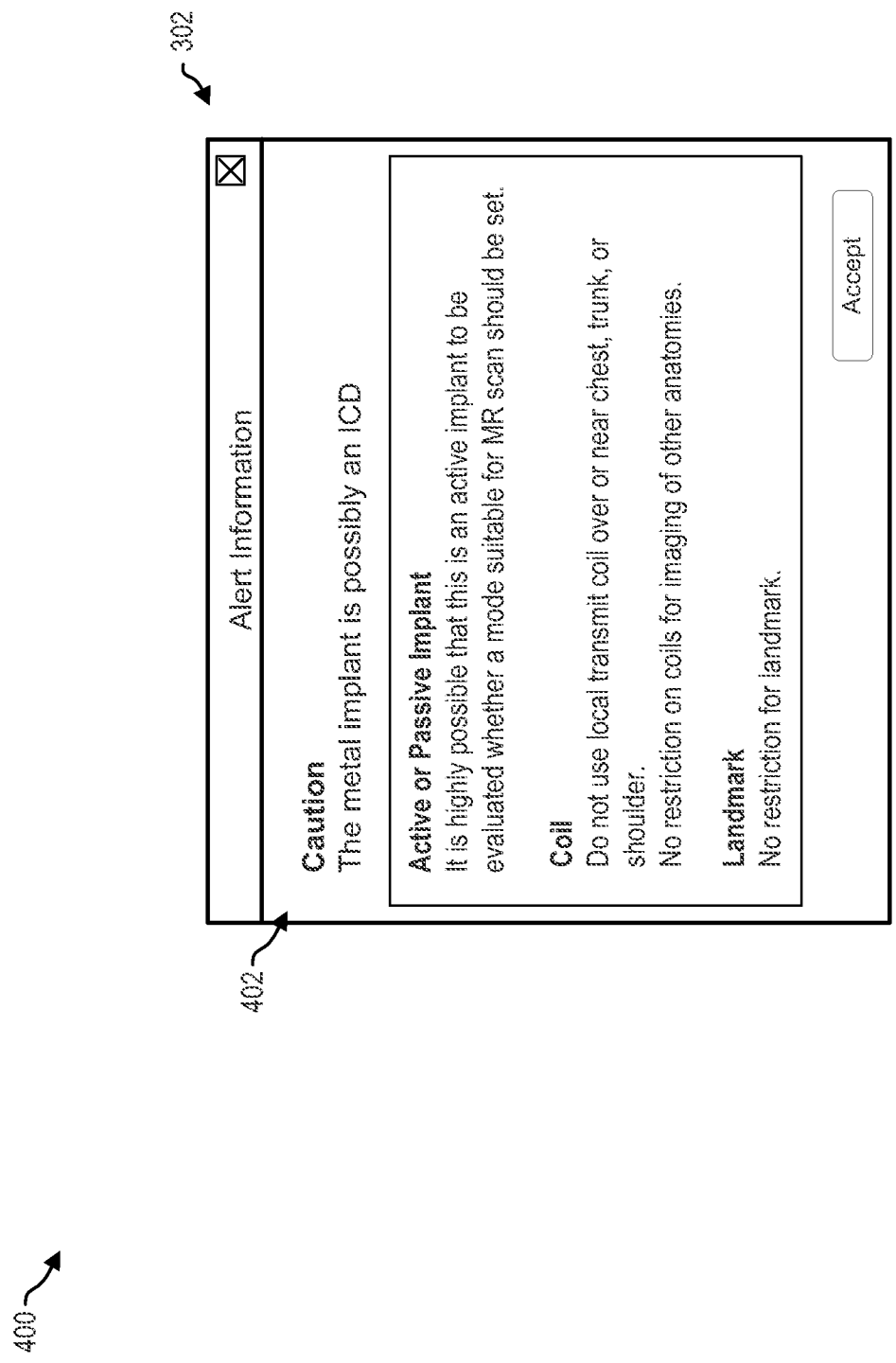
FIG. 4 shows a second image of the user interface illustrating pre-screen alerts.
Figure 5:
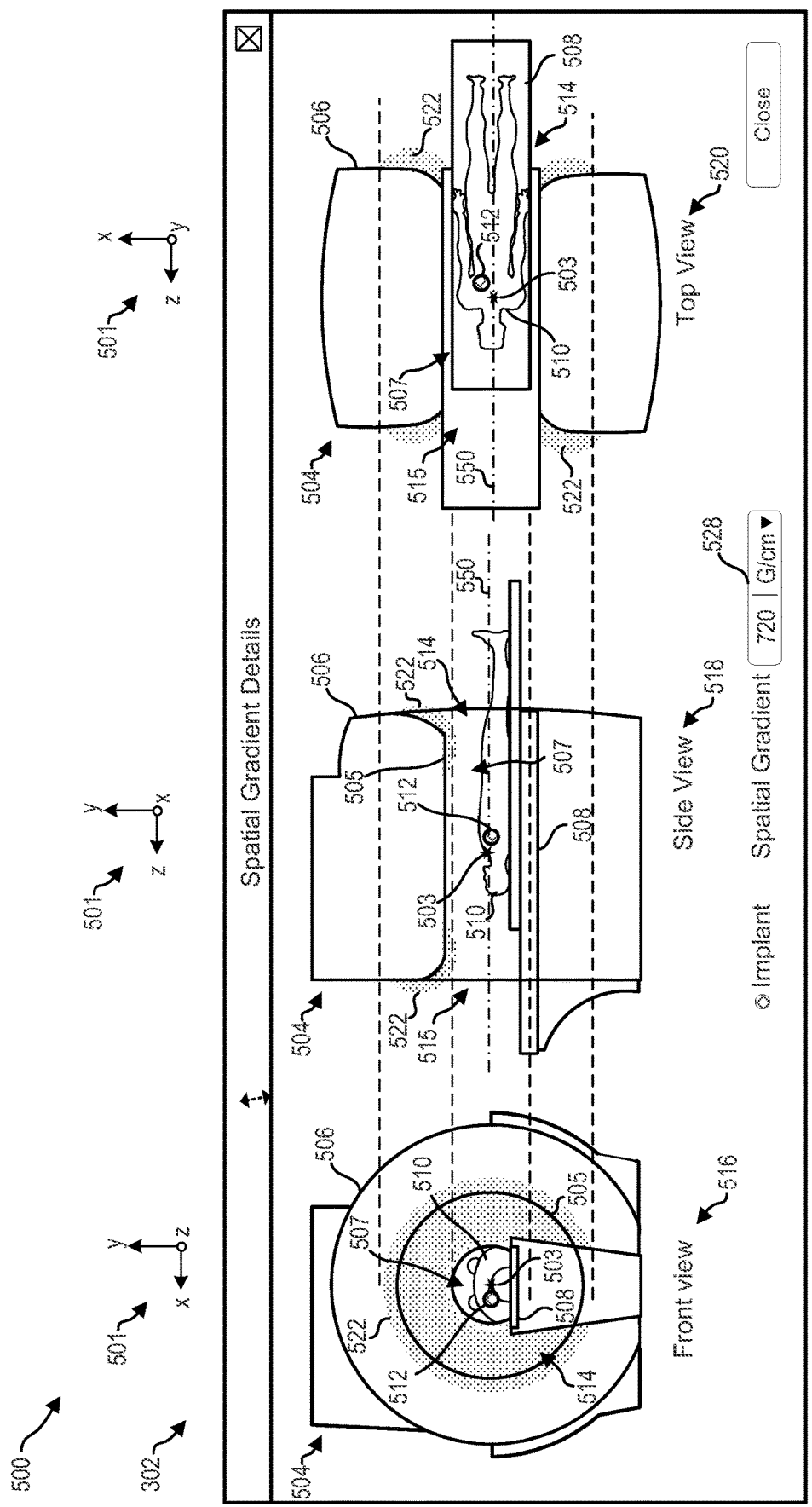
FIG. 5 shows a third image of the user interface illustrating a magnetic spatial gradient of an MRI scanner relative to an implant in a patient.

The following description relates to various systems and methods for magnetic resonance imaging (MRI) patient pre-screening. In particular, methods are provided for locating and identifying implants in a patient as well as obtaining a model of the patient's body prior to performing MRI scanning. An MRI system may be used to gain information regarding a patient's tissues and organs. However, presence of an implant in a patient may preclude the patient from MRI or demand scanning parameters (e.g., magnetic spatial gradient limit) to accommodate potential interactions of the implant with a magnetic field, which may adversely affect the patient. The MRI system may be paired with a pre-screen system to determine presence, location, and identity of an implant prior to MRI operation. The information obtained by the pre-screen system may be communicated to the MRI system via a communication link and/or stored in a database accessible by the MRI system, as shown in FIG. 1. The pre-screen system may include various detection devices embedded into an entryway to an MRI scanning room, as shown in a schematic diagram of an MRI image center illustrated in FIG. 2. A first image of a user interface of an MRI computing system is shown in FIG. 3 indicating location of an implant detected in the patient and corresponding alerts providing scanning instructions are shown in a second image of the user interface in FIG. 4. In FIG. 5, a third image of the user interface shows a spatial gradient of an MRI scanner relative to a patient's implant, providing a guide for adjusting operation of the MRI scanner to accommodate the implant. Methods for implementing pre-screen modalities to identify and locate implants in a patient and adjust scan parameters accordingly are shown in a high-level flowchart in FIG. 6 and a detailed flowchart in FIG. 7.

Magnetic resonance imaging is a powerful tool allowing diagnostic imaging of tissues and organs based on exposure of a subject to a magnetic field. For example, an MRI apparatus includes a superconducting magnet which generates a strong, uniform, static magnetic field $B_0$. A metallic object subjected to the magnetostatic field $B_0$ may itself become magnetized. In particular, medical implants having metallic components may be affected by exposure to the magnetostatic field and, in some examples, may lead to disruption of implant operation, dislocation of the implant and/or heating of the implant. Thus detecting and identifying implants in subjects prior to MRI scanning may circumvent such issues. In some instances, however, patients may not remember specific details as to the location or identity of an implant and detection of the implant solely by, for example, a metal detecting device may not provide sufficient information to determine whether the patient is suitable for MRI or to adjust MRI operating parameters to accommodate a placement and a type of implant.

The issues described above may be at least partially addressed by implementing a pre-screen procedure to be performed prior to MRI scan of a subject. In one example, the pre-screen procedure includes scanning the subject with a scanning apparatus positioned a certain distance away from an MRI scanner. Information obtained via the scanning apparatus may be used to determine if and how operation of the MRI apparatus may proceed, depending on location and identification of an implant.

FIG. 1 shows a block schematic diagram of an exemplary embodiment of an architecture 100 for MRI pre-screening, which comprises an MRI system 102 connected to a pre-screen system 150. The MRI system 102 may be positioned remote relative to the pre-screen system 150. Thus the pre-screen procedure may be performed by the pre-screen system 150 prior to the MRI scan by the MRI system 102. The pre-screen procedure may be performed to assess whether the subject is suitable for subsequent scanning by MRI.

The MRI system 102 includes a controller unit 25, a MRI scanner 30, a data processing unit 31 and a user interface 33. A processor 103 and a non-transitory memory 104 may be included in the controller unit 25. The non-transitory memory 104 stores executable instruction that when executed by the processor 103 cause the processor 103 to perform various actions with respect to obtaining an MRI scan.

The MRI scanner 30 may be any appropriate MRI scanner known in the art, which generally includes magnet, gradient coils and drivers, RF transmit and receive coils, RF chain, and so on, for scanning a subject. In particular, a static magnetic field $B_0$ is formed by a magnetostatic field magnet unit of the MRI scanner. Encoding gradients are formed by gradient coils, under control of the controller unit 25, to encode spatial information. RF transmit coil transmits, under control of the controller unit 25, an excitation RF pulse to a subject positioned in the static magnetic field $B_0$, which, in response, produces the magnetic resonance signal. The signal is received by the RF receive coil and may be further processed to produce MR images.

The data processing unit 31 may include one or more processors and a recording medium which stores instructions to be executed by the processor(s) to perform data processing. The data processing unit 31 may apply various image processing operations to the magnetic resonance signals acquired by the MRI scanner 30.

The user interface 33 may include a display device which displays images and other information on the display screen. The user interface 33 may display, for example, operation data, patient information, etc. for performing an MRI scan. The user interface 33 may also display two-dimensional (2D) images and/or three-dimensional (3D) images of the subject 16 generated by the data processing unit 31.

The user interface 33 of the MRI system 102 is also configured to receive input from an operator of the MRI system 102 as well as display information. To that end, user interface 33 may comprise one or more of an input device, including but not limited to a keyboard, a mouse, a touch-screen device, a microphone, and so on, and an output device, including but not limited to a display device, a printer, and so on.

The pre-screen system 150 may be communicatively coupled to the MRI system 102 via a wired or wireless connection. The pre-screen system 150 may include a processor 106 and a non-transitory memory 108. The non-transitory memory 108 stores executable instructions that cause the processor 106 to command operation of one or more pre-screen modalities to gain information about a presence (or lack thereof) of an implant in a subject or provide a body model of the subject. The information regarding the implants and the body model of the subject may be obtained via a full-body scanner equipped with one or more pre-screen modalities. The full-body scanner may be arranged in a remote location relative to the MRI system 102, e.g., positioned a certain distance away from the MRI system 102. The pre-screen modality may be one of a variety of detection methods, including terahertz (THz) scanning, electromagnetic induction, as well as other types of detection methods, described further below with reference to FIGS. 3-8.

The pre-screen system 150 further comprises at least one scanner 110 for scanning a subject, such as a patient, to acquire data, such as imaging data, thermal data, metal detection, etc. Depending on the type of pre-screen system, the scanner 110 may comprise multiple components for scanning the subject. For example, if the pre-screen system comprises an ultrasound imaging system, the scanner 110 may comprise an ultrasound transducer. Thus, the term "scanner" as used herein refers to the components of the imaging system which are used and controlled to perform a scan of the subject.

The type of data acquired by the scanner 110 also depends on the type of pre-screen system 150. For example, if the pre-screen system 150 comprises an ultrasound imaging system, the imaging data acquired by the scanner 110 may comprise analog and/or digital echoes of ultrasonic waves emitted into the subject by the ultrasound transducer.

The pre-screen system 150 may further comprise a camera 112 for assisting with the automatic positioning of the subject within the pre-screen system 150. For example, the camera 112 may capture live images of the subject within the imaging system, while the processor 106 determines a position of the subject within the imaging system based on the live images.

The architecture 100 may further comprise one or more external databases 116 that the pre-screen system 150 and the MRI system 102 may be communicatively coupled to via a network 118. The one or more external databases 116 may comprise, as exemplary and non-limiting embodiments, one or more of a hospital information system (HIS), a radiology information system (RIS), a picture archive and communication system (PACS), and an electronic medical record (EMR) system. The MRI system 102 and/or the pre-screen system 150 may retrieve information such as subject metadata, which may include metadata describing or relating to a particular subject to be scanned (e.g., patient age, gender, height, and weight), which may be retrieved from an EMR for the subject.

The architecture 100 may further comprise a repository 120 communicatively coupled to one or more of the MRI system 102 and the pre-screen system 150 via the network 118. The repository 120 stores implant database storing various properties of various types of implants. Information about the types of implants may be provided by manufacturers and entered into the repository 120 as downloadable libraries or registries. Additionally or alternatively, information about each implant may be manually entered by the operator. In some embodiments, the implant database may be stored in the MRI system 102 rather than a separate repository.

Figure 2:
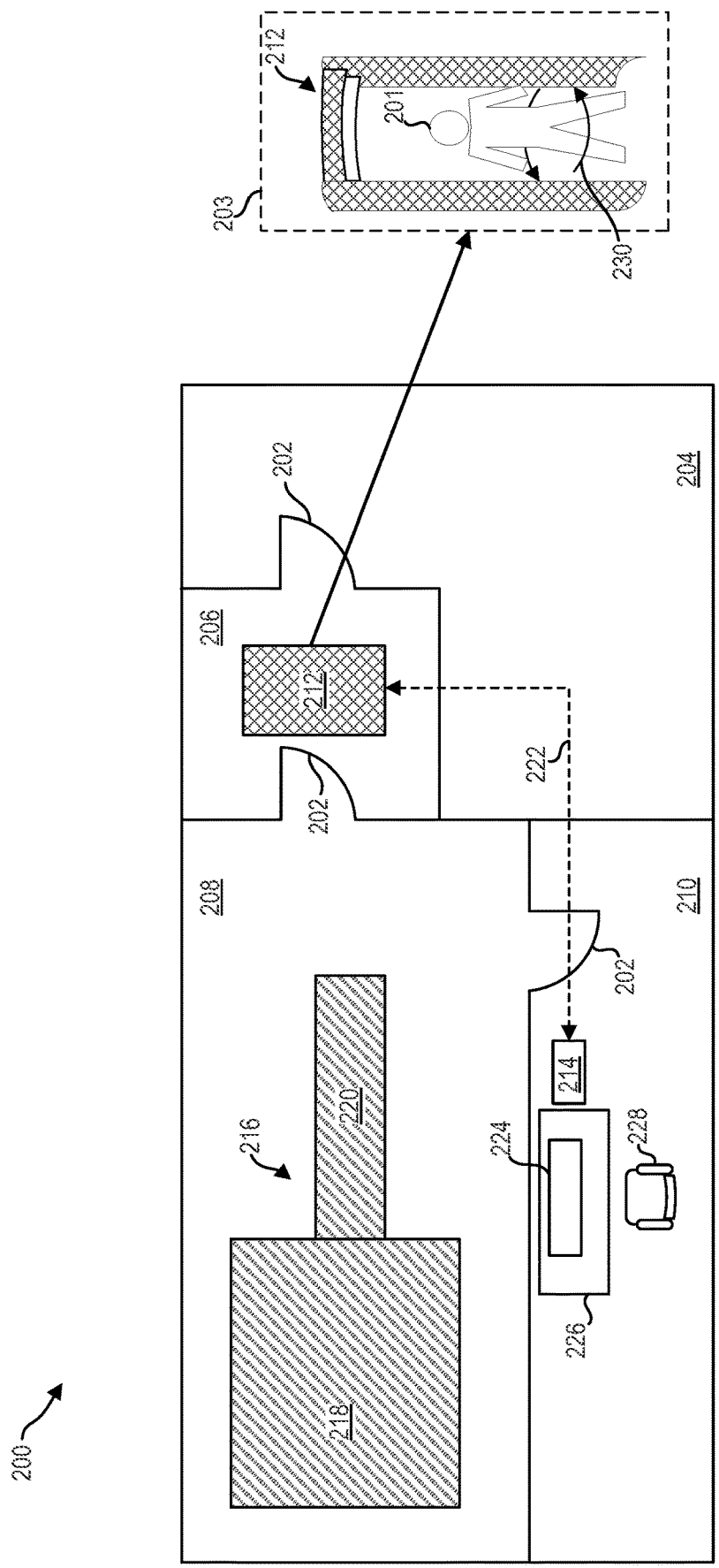
FIG. 2 shows a schematic diagram of an MRI imaging center according to an exemplary embodiment.

An MRI system and a pre-screen system, such as the MRI system 102 and the pre-screen system 150 of FIG. 1, may be located in an MRI imaging center 200 as shown in FIG. 2. The MRI imaging center 200 may be configured with a plurality of rooms interconnected by a plurality of doorways 202, the plurality of rooms including a patient waiting area 204, a staging room 206, a scanning room 208, and an operator room 210.

A subject 201 may first enter the Mill imaging center 200 through the patient waiting area 204. The subject 201 may pass through one of the plurality of doorways 202 to enter the staging room 206 in which a screening scanner 212 may be disposed. The screening scanner 212 may correspond to the scanner 110 of the pre-screen system 150 in FIG. 1. A perspective view of the screening scanner 212 is shown in insert 203. The screening scanner 212 may be a full-body scanner that the subject 201 may walk through prior to entering the scanning room 208 through another doorway of the plurality of doorways 202. The subject 201 may be instructed to stand in the screening scanner 212 and remain motionless for a duration of time, such as 10 seconds. When the subject 201 is standing in the screening scanner 212, e.g., positioned in an opening and at least partially surrounded by the scanner 212, a suite of scans and analyses may be performed to determine if the subject 201 has an implant, such as a medical implant. The suite of scans and analyses may include methods of detection such as THz technology, metal detection, thermography, ultrasound imaging, etc., where the methods of detection enable detection, identification, and location of the medical implant. Further details of the screening scanner 212 and methods of detection are described further below, with reference to FIGS. 3-7.

The screening scanner 212 may be magnetically shielded and/or maintained a certain distance from an Mill scanner 216 positioned in the scanning room 208. The MRI scanner 216 may correspond to the MRI scanner 30 of the MRI system 102 in FIG. 1. In other words, the screening scanner 212 is a remote device with respect to the MRI scanner 216. For example, a location of the screening scanner 212 within the staging room 206 may be varied based on a distance of the MRI scanner 216 from the doorway of the plurality of doorways 202 between the staging room 206 and the scanning room 208. Additionally or alternatively, a wall separating the staging room 206 from the scanning room 208 may include magnetically shielding material or the wall may have an increased thickness to block penetration of a magnetic field generated in the scanning room 208 into the staging room 206 or block penetration of a radio frequency field generated by the MRI scanner 216 during operation into the staging room 206. Furthermore, the MRI scanner 216 may be positioned within the scanning room 208 so that a 5 gauss line is maintained within the scanning room 208.

Data obtained by the screening scanner 212 may be sent to the controller 214 located in the operator room 210. In some embodiments, the controller 214 may control operations of both the screening scanner 212 and the MRI scanner 216. In some embodiments, the controller 214 controls the operation of the MRI scanner 216 and is in communication with a controller (e.g., 106 and 108 in FIG. 1) that controls the operation of the screening scanner 212. The controller 214 may correspond to the controller unit 25 of FIG. 1, communicating with a control system of the screening scanner 212 via a communication link and/or a network, as indicated by arrow 222. Data received at the controller 214 from the screening scanner 212 may be used to guide a scanning procedure of the subject 201 by Mill. The MRI scanner 216 may have a magnet assembly 218 and a bed 220. The subject 201 may be scanned to obtain information about specific tissue regions or organs.

The scanning room 208 may be linked to the operator room 210 by another doorway of the plurality of doorways 202. The operator room 210 may house the controller 214, a display device 224, such as a monitor, supported on a table 226, and an operator chair 228. The display device 224 may also serve as a user interface, allowing the operator to input instructions and information which are relayed to the controller 214. The operator room 210 and the staging room 206 may be magnetically shielded to mitigate interference of any ferromagnetic objects in the operator room 210 and/or the staging room 206 with a magnetic field generated at the MRI apparatus 216 during scanning.

A pre-screen procedure, utilizing the screening scanner 212 to perform one or more pre-screen modalities, may be implemented in the staging room 206 when the subject 301 is positioned in the opening of the screening scanner 212. The pre-screen may be conducted as the subject 201 walks through the screening scanner 212. Thus information about the implant, instructions specific to placement of a magnetic field relative to the implant, and recommendations for positioning of the subject 201 in the MRI scanner 216 may be provided to an operator as the subject 201 approaches the scanning room 208 and prior to preparing the subject 201 for MRI. The pre-screen procedure allows detection of a presence of the implant, circumventing issues arising from presence of an unreported implant or incomplete or incorrect information provided to the operator. Furthermore the operator may be alerted to a ferromagnetic property of the implant or a sensitivity of the implant to magnetic spatial gradient during pre-screening.

The pre-screen procedure may include, as described above, various imaging and detection modalities to provide information about any implant present in an MRI subject. Parameters of the MRI scan may be adjusted to accommodate the implant or, if the implant is determined to be ferromagnetic, MRI may be precluded. The modalities incorporated in the pre-screen procedure may include rapid analyses, e.g., conducted within several seconds or less, which may be enacted without additional preparations performed by the subject, e.g., the pre-screen procedure may be implemented without removal of the subject's clothing.

In some embodiments, a pre-screen procedure may include a combination of THz technology and electromagnetic induction to obtain a three-dimensional (3-D) body model and detect presence of an implant, respectively. THz technology utilizes electromagnetic radiation between 0.1-10 THz, e.g., the THz gap. THz rays are non-ionizing and penetrate clothing, polyethylene, polyester but cannot pass through metal. A screening scanner, such as the screening scanner 212 of FIG. 2, may be adapted with at least two antennae which rotate around a subject, as indicated by arrows 230 in FIG. 2. Wave energy is reflected back from the subject and used to construct a three-dimensional image of the subject. The image depicts the implant within 2 cm of an actual location of the implant. The image generated by reflected THz rays may be displayed on a display device, such as the display device 224 of FIG. 2.

A high sensitivity of THz technology to metal, arising from impenetrability of metals to THz waves, enables effective detection of metals outside of the body, thereby enabling removal of external metal objects carried by the subject prior to the subject entering the scanning room 208. THz waves do not penetrate skin, therefore exposure of the subject to THz radiation does not adversely affect the subject. However, THz waves penetrate through fabric, e.g., clothing, and may therefore be applied without removal of clothing. In addition, by imposing a maximum magnetic field of 20 µT (0.2 Gauss) in the THz instrumentation, the implant inside the subject is also not affected by THz radiation. A full body image of the subject may be obtained in a short period of timer, such as 1.5 seconds or less.

Electromagnetic induction may be used in addition to THz technology to detect a presence of a metal in the subject, e.g., as a metal detector. The metal detector may include a transmitter coil configured to generate a magnetic field when a current is applied to the transmitter coil. The magnetic field produced at the transmitter coil may be reflected by a metal object, such as a medical implant, passing through the magnetic field, producing a reflected magnetic field. The reflected magnetic field may react with a receiver coil, causing a current to pass through the receiver coil. The current generated by the reflected magnetic field may trigger an alert or indicator to an operator of a presence of the metal object in the subject. Furthermore, the metal detector may be adapted with zones that enable location of the metal object relative to the subject's body and provide a rough outline of a shape of the metal object through filtered back projection reconstruction. Electromagnetic induction may provide highly sensitive metal detection, capable of detecting a metal object as small as half of a paperclip.

The signal obtained by electromagnetic induction, e.g., the current produced by the reflected magnetic field, may have a positive correlation with distance between sensors of the metal detector and the metal object passing through. The metal detector may rotate around the subject, similar to the antennae of the THZ technology and indicated by arrows 230 in FIG. 2, to acquire a 360 degree scan of the subject. A multiple area alert may be displayed at the user interface if more than one metal object is detected. The metal detector may also be configured to determine a metallic content of the metal object, e.g., whether the metal is ferromagnetic or non-ferromagnetic.

The combination of THz technology and electromagnetic induction may provide a highly sensitive, efficient suite of pre-screen modalities for a pre-screen procedure to rapidly detect the presence of an implant in a subject. A location of the implant may be mapped via the image of the subject's body obtained through THz technology and identification of the metal may be provided by electromagnetic induction. The pre-screen procedure may thereby accommodate any subject and any type of implant. Information gained through the pre-screen procedure may enable a controller of an MRI scanner to identify the implant type and provide instructions based on the information regarding positioning of the subject, suitable spatial gradient threshold for the detected implant, and energization of coils specific to landmarks, e.g., anatomical structures with distinguishable morphological characteristics.

The acquired pre-screen data may be matched to an implant database storing various properties of various types of implants, such as information from manufacturers of the implants. A geometry of the implant may be compared to three-dimensional shapes of implants in the database to identify the type of implant detected in the subject. By matching the detected implant to an implant in the database, the implant may be assessed for compatibility with MRI. An implant with ferromagnetic material, for example, may preclude the subject from MRI. For non-ferromagnetic implants, suitable scanning parameter(s) may be determined based on the identity of the implant, additional preparation or post-examination procedures may be provided, spatial gradient tolerance, and coil and landmark parameters may be set based on stored information in the implant database.

In some embodiments, a controller unit, such as the controller unit 25 of FIG. 1 and the controller 214 of FIG. 2, may receive data from a pre-screen procedure and display the information as shown in a first image 300 that may be shown at a user interface 302 as depicted in FIG. 3. The user interface 302 may correspond to the display unit or user interface 33 of FIG. 1. An anatomical image 304 may be displayed on the user interface 302 with an implant 306 positioned in the anatomical image 304. A location of the implant 306 in the anatomical image 304 may represent a location of a detected implant in a subject determined via the pre-screen procedure. For example, the anatomical image 304 may be obtained by the THz technology and the implant 306 may be detected by the electromagnetic induction technology. The implant 306 may be overlaid on or inserted to the anatomical image 304 through an image registration process, using technologies known in the art. A rough three-dimensional shape of the implant 306 may also be shown if acquired by the pre-screen procedure.

A list of anatomical regions 308 is shown at the user interface for the operator to select an appropriate scanning protocol. A tab 310 labelled "Chest" in the list of anatomical regions 308 may be selected, resulting in display of a set of pulse sequences that can be used to scan the chest. Similarly, selection of other tabs of the list of anatomical regions 308 provides pulse sequence sets specifically for scanning the selected anatomical region.

An operator may click on the implant 306, using a cursor, for example, to open an implant database or library. Opening the implant library may display implants grouped according to a category based on anatomical location and/or selected filter of the implant. Images of each of the implants may be displayed. In some embodiments, an operator may choose an implant image that matches the three-dimensional outline of the detected implant 306. In some embodiments, similarities of implants in the database to the detected implant may be ranked automatically for the operator to review. Upon selecting the implant image, properties and additional processes corresponding to exposure of the implant to MRI may be shown, as depicted in a second image 400. The second image 400 may also be shown at the user interface 302.

The second image 400 is an alert message 402 relaying cautionary information to an operator. The alert message 402 may include a suggestion of an identification of the implant, e.g., the implant 306 of FIG. 3. In FIG. 4, the alert message 402 indicates the implant may be an active implant, such as an implantable cardioverter defibrillator (ICD). Additional guidance is also provided, including a suggestion for further preparation of the implant by adjusting a mode of the implant to enable MR scanning, guidelines for local energization of a transmit coil relative to the implant and corresponding region of the subject's anatomy, as well as operating parameters regarding landmarks. The alert message 402 may relay data from the implant database associated with the specific type of implant, enabling suitable adjustments to be made for the implant.

Identification of the implant may occur via alternative routes. The subject may inform the operator prior to the pre-screen procedure of the type of implant and the operator may search the implant database for a matching implant data folder by entering the name, model, or some other identifying information of the implant at the user interface 302, into a search field or search bar, for example. The operator may select the implant from the list of implants displayed upon searching and obtain information provided in the alert message 402 relevant to the specific implant.

In some embodiments, if an exact match to the implant 306 based on shape and location is not found, the operator may choose an option to use a spatial gradient limit that is compatible with any type of implant. The controller unit may refer to information and instructions stored in a memory of the controller unit and display instructions for setting the spatial gradient limit as well as additional procedures and adjustments to MRI operating parameters pertaining to a conservative MRI approach based on the unidentified implant. In some embodiments, the speed of patient table movement may be determined based on the spatial gradient limit according to a known relationship. In some instances the operator may choose to not perform MRI on the subject when the implant is not identifiable but determines the implant may have a high likelihood of poor magnetic field tolerance.

When information provided by the pre-screen procedure confirms that the subject is to proceed with MRI, instructions for an MRI procedure accommodating the detected implant may be provided to guide the scan. Operating parameters of the MRI scanner may be adjusted for each subject and each type of implant, if present in the subject. Information obtained via the pre-screen procedure may be used to provide recommendations as to specific MRI parameters, which may be displayed on the user interface, as shown in FIG. 5 in a third image 500 of the user interface 302. A set of references axes 501 is provided for comparison between views shown, indicating a y-axis, an x-axis, and a z-axis. The y-axis may be parallel with a direction of gravity. The user interface 302 may show a schematic representation of an MRI scanner 504, including a magnet assembly 506 and a slidable patient table or bed 508. An image of a subject 510 with an embedded implant 512 may be depicted on the bed 508, the bed 508 configured to slide in and out of a bore 514 of the magnet assembly 506. The image of the subject 510 may be a graphic display of body model of the subject based on data obtained via THz technology, as described above.

The MRI scanner 504 is shown from a front view 516, a side view 518, and a top view 520. A positioning of the implant 512 in the subject 510 may reflect a location of the implant 512 as determined by the pre-screen procedure, e.g., by THz technology and electromagnetic induction. The user interface 302 may show a maximum magnetic field spatial gradient value 528 as tested. Depending on a sensitivity of the implant 512 to a spatial gradient, the speed of the bed movement may be changed to accommodate the implant 512.

The "fringe field" of the MR scanner creates a spatial gradient magnetic field. The spatial gradient describes how the intensity of the static magnetic field, e.g., the magnetic field generated by the magnet assembly 506, changes over spatial distance. The isocenter 503 of the magnet assembly 506 may be centered along a central axis 550. The spatial gradient may be largest close to the edge of the bore of the magnet assembly 506, as indicated by shaded areas 522 depicted in FIG. 5. When a metal implant moves in the spatial gradient magnetic field, current may be induced in the implant.

The subject 510 may be arranged in a horizontal position, e.g., prone or supine. When being moved in and out of the bore, the subject 510 carrying the implant 512 may pass the shaded areas 522 where the spatial gradient may be large (e.g., close to the maximum spatial gradient). The controller unit may utilize an identity and location of the implant 512 as well as a 3-D body model representing actual dimensions of the subject 510 acquired from the pre-screen procedure to determine a suitable table movement speed to ensure the safety of the patient with the implant when moving in/out of the bore. As such, the user interface 500 provides visual instructions to an operator that shows where the spatial gradient magnetic field are located relative to the MRI scanner 504 and the subject 510, e.g., the shaded areas 522, as well as recommendations for table movement speed and/or positioning of the subject 510. For example, the spatial gradient values to which the implant 512 is exposed may be reduced by maintaining the implant 512 within a region centered along the central axis 550.

The controller unit of the MRI scanner 504 may be configured to display additional information based on the pre-screen procedure. For example, the additional information may include any additional actions for an operator to prepare the subject 510 and the implant 512 for MRI, such as removing a removable ferromagnetic implant or adjusting an operating mode of an adjustable implant to a suitable mode for MRI. The additional information may further include guidelines for activation of RF coils, use of landmarks, and placement of the subject 510 on the bed 508, based on the body model acquired from the pre-screen procedure and displayed on the user interface 302. The user interface 302 may also display parameters for speed of bed movement, display error messages if incorrect RF coils are chosen by the operator to activate, and highlight anatomical regions of the subject 510 which are precluded from being landmarks.

It should be understood that any appropriate modalities may be implemented in the pre-screen procedure. Some embodiments may be adapted with infrared thermography, for example, to obtain a thermal image of a subject. A presence of a metal object, such as an implant, in the subject produces a distinct thermal pattern. A body model and implant location may be acquired rapidly by infrared thermography and may provide data to supplement information obtained via THz technology and electromagnetic induction, or used independently to map the implant in the subject. Infrared thermography is not obstructed by clothing and may also deliver information regarding tissues and organs surrounding the implant. The thermal image generated may indicate a length of time that the implant has been embedded. As MRI is not recommended within several weeks of insertion of the implant, the thermal image may be used to evaluate if the tissues and/or organs near the implant are sufficiently healed.

Ultrasound may also be used to detect presence of an implant. Metal may reflect ultrasound radiation differently from tissue and may be readily observed. In some embodiments, an ultrasound detector may be installed in a scanning room, e.g., the scanning room 208 of FIG. 2, either as a separate device from an MRI apparatus or integrated into the MRI apparatus by embedding the ultrasound detector into a bed of the MRI apparatus. Ultrasound may also be used to evaluate a condition of tissue surrounding the implant, e.g., an extent of tissue healing around the implant.

A Hall sensor may be used to detect metal, including ferromagnetic metals. An array of Hall sensors may detect an entire body outline of a subject as well as presence of an implant. The array may include Hall sensors of varying sensitivity, with at least one Hall sensor to obtain the outline of a subject and at least one Hall sensor to detect the implant. The array of Hall sensors may be positioned at a pre-screen apparatus, such as the screening scanner 212 of FIG. 2 to scan the subject when the subject stands in an opening of the pre-screen apparatus.

Two-dimensional (2D) photography may be used in combination with oral inquiry of a subject to acquire a 3-dimensional (3D) body model of the subject. 2D photographs of the subject may be taken from different angles using various types of cameras. The photographs may be uploaded to a controller unit of an MIll apparatus and used to modify a generic body model to more accurately represent a shape of the subject. The operator may query the subject for presence of an implant and location of the implant if present. Use of 2D photography in combination with oral inquiry may be a low cost but less efficient routine for conducting a pre-screen procedure, incorporating at least two actions.

A 3D model of a subject may also be generated by a Kinect sensor. By positioning a subject in front of the Kinect sensor, the 3D model may be created immediately, reducing an amount of time spent obtaining the 3D model compared to compiling 3D photographs. The Kinect sensor may also be incorporated into a pre-screen apparatus and presence of an implant in the subject may be determined by oral inquiry.

Figure 6:
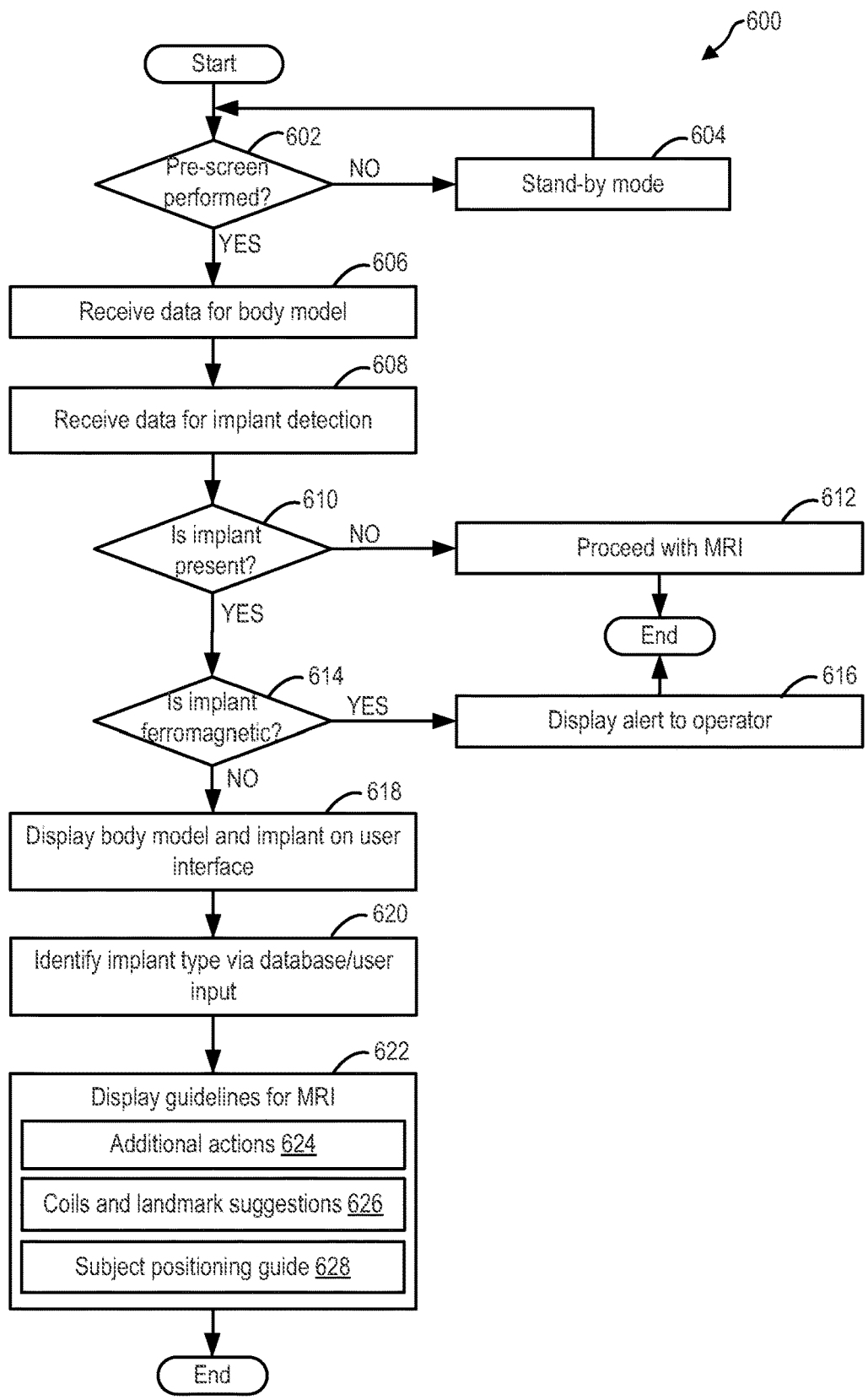
FIG. 6 shows a first, high-level flowchart illustrating an example method for MRI pre-screen according to an embodiment.
Figure 7:
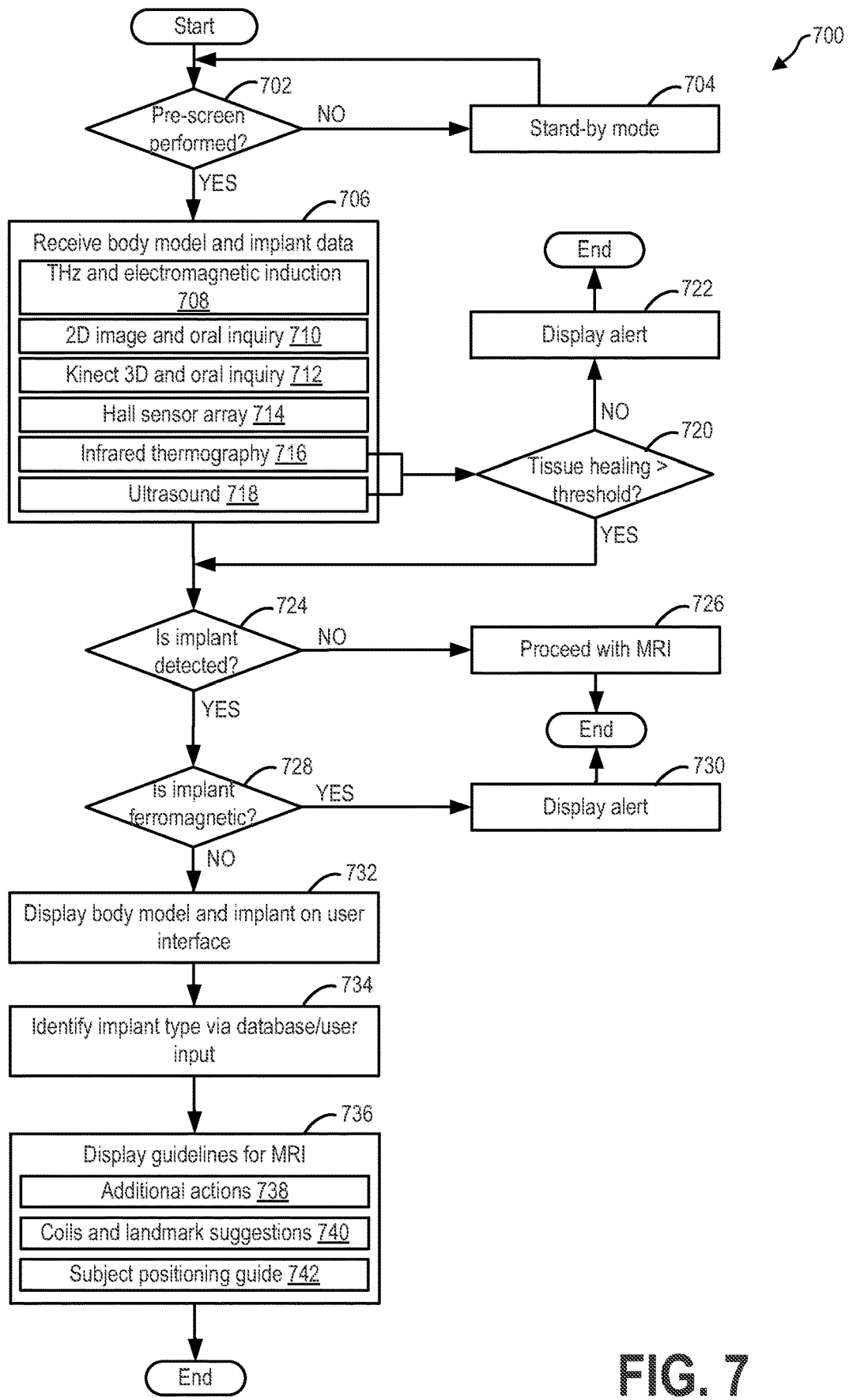
FIG. 7 shows a second, detailed flowchart illustrating an example method for MRI pre-screen according to an embodiment.

The methods described above may be used in addition to or as alternatives to THz technology and electromagnetic induction. Various combinations of the methods have been contemplated. In some instances, one or more methods for implant location and metal detection may be paired with at least one method for assessing tissue condition at an implant. A first exemplary embodiment of a pre-screen routine 600 is shown in FIG. 6 and a second embodiment of the pre-screen routine 700 is shown in FIG. 7. The first pre-screen routine 600 is a high-level flowchart describing a plurality of steps performed prior to preparing the subject for MIll. The second pre-screen routine 700 describes details of pre-screen modalities which may be implemented in a pre-screen routine to identify and locate the implant in a subject. The first and second pre-screen methods 600, 870 are described with regard to the systems and components of FIG. 2, and, in particular, with detection and imaging devices embedded into the screening scanner 212 arranged in the staging room 206 of FIG. 2. The screening scanner may be a full-body scanner located in a remote location relative to an MIll scanner and a controller unit of the MRI scanner. The embedded devices may be communicatively linked to the controller unit configured with an implant database stored in a memory of the controller unit, where the implant database includes a list of implants and information specific to each of the implants, as provided by manufacturers of the implants. Methods 600 and 700 may be implemented as executable instructions in non-transitory memory of the controller unit, for example.

In the first pre-screen method 600 of FIG. 6, it is determined whether the subject has been prescreened via the screening scanner at 602. The controller unit may query a controller of the screening scanner to determine if new data is stored in a memory of the controller of the screening scanner. If new pre-screen data is not found at the controller of the screening scanner, the controller unit is on stand-by, e.g., adjusted to a stand-by mode at 604, and the method returns to the start. If new data is found at the controller of the screening scanner, the controller unit of the MRI receives information for constructing a 3-D body model of the subject from the new data at 606. The controller unit further receives information confirming presence of an implant in the subject at 608.

Presence of the implant is confirmed at 610. If no implant is found, affirmation that an MRI procedure may proceed is displayed on a user interface of the MRI system, such as the user interface 302 of FIGS. 3 and 4, at 612. The method ends. If the implant is detected, it is determined whether the implant is ferromagnetic at 614. If the implant is ferromagnetic, an alert is displayed on the user interface at 616. Generation of the alert may inhibit activation of the MRI scanner so that an operator may not command operation of the MRI scanner. The method ends.

If the implant is not ferromagnetic, the 3-D image, or body model, of the subject is displayed at the user interface at 618. The body model reflects a height and size of the subject. The detected implant is also displayed at 618, shown in a position in the body model that represents an actual location of the implant in the subject. At 620, the implant is identified by analysis with an implant database. Information regarding the implant may be manually entered by operator or the controller unit may be configured to match the implant through a registration system to of the list of implants stored in the controller unit's memory, based on location and implant shape. Alternatively or additionally, the controller unit may be configured to identify the implant via machine learning in a system adapted with a deep neural network.

In instances where the implant is not matched to an implant in the implant database, a nominal set of MRI operating parameters may be used. The nominal operating parameters may be pertaining to a conservative MRI approach based on the unidentified implant. An alert notifying the operator that the implant is not matched and that the nominal operating parameters are recommended may be displayed on the user interface. Additionally, an option may be provided to the operator to enter information regarding the unidentified implant if, for example, an implant manual is obtained for the implant. The implant may be added to the implant database for future reference.

Guidelines and alerts for the MRI procedure are displayed on the user interface at 622. The guidelines may include recommendations for additional preparation of the subject and/or implant at 624 such as adjusting a mode of the implant to a suitable mode for MRI, removing the implant if removable, removing removable ferromagnetic parts of the implant, etc.

The guidelines may also include suggestions for localized energization of RF coils or use of particular landmarks specific to the type of implant at 626 based on identification through the implant database. Instructions for table movement speed and/or positioning of the subject may be shown at 628. The method ends.

Turning now to the second pre-screen method 700 of FIG. 7, it is determined whether the subject has been scanned via the screening scanner at 702. The controller unit may query a controller of the screening scanner to determine if new data is stored in a memory of the controller of the screening scanner. If new pre-screen data is not found at the controller of the screening scanner, the controller unit is on stand-by, e.g., adjusted to a stand-by mode at 704, and the method returns to the start. If new data is found at the controller of the screening scanner, the controller unit of the MRI receives data for constructing a 3-D body model of the subject and detecting an implant at 706.

Receiving data may include receiving information via THz technology to obtain a 3-D body model of the subject and electromagnetic induction to identify presence of an implant at 708. THz antennae and a metal detector using electromagnetic induction may be embedded in the pre-screen apparatus. A location and shape of the implant may be determined by electromagnetic induction, as well as a type of metal, e.g., ferromagnetic vs. non-ferromagnetic, in the implant. Additionally or alternatively, 2-D images may be obtained by photography (e.g., using a camera) and information regarding presence and/or location and identity of the implant may be acquired by asking the subject at 710. An operator may photograph the subject at a suitable location, e.g., in a staging room or waiting area of an MRI imaging center, such as the MRI imaging center 200 of FIG. 2. The 2-D images may be compiled to generate a 3-D body model of the subject. Similarly, at 712, the 3-D body model may be obtained directly via Kinect 3D scanning, where a Kinect sensor is embedded in the pre-screen apparatus, and the presence, location, and identity of the implant confirmed by questioning the subject. Both the 2-D imaging and the Kinect 3D scanning may be preferentially supplemented by a technique for detecting metallic objects, such as electromagnetic induction, to accommodate instances where the subject may not remember the presence, location, and/or identity of the implant.

Receiving data may also include utilizing a Hall sensor array at 714 to obtain an outline of the subject to create the 3-D body model and detect presence of the implant. The Hall sensor array may include more than one sensor of differing sensitivities, incorporated into the pre-screen device, the more than one sensor enabling identification of ferromagnetic materials in the subject in addition to generating the 3-D body model. A sensitivity of the Hall sensor array may be dependent on a ratio of a size of the implant relative to a size of the subject, thus, the Hall sensor array may be preferentially used in combination with another pre-screen modality able to accommodate a wide range of subject sizes.

Infrared thermography may be used at 716 to obtain a thermal image of the subject by embedding an infrared camera in the pre-screen apparatus. The thermal image may indicate the presence and location of the implant based on differences in thermal patterns. The 3-D body model and implant location may be determined as well as a condition of tissue surrounding the implant. Information regarding a healing of the tissue may be obtained, indicating whether the tissue is ready for exposure to MRI and/or a duration of time since the implant was inserted. Infrared thermography may be less effective when the implant size to subject size ratio is smaller than a threshold or when the implant is embedded deep inside the subject. Thus, infrared thermography may be used in combination with another, more robust pre-screen modality.

Ultrasound may be also be received at 718. An ultrasound detector may be incorporated into the screening scanner, arranged in the staging room as a unit independent from the screening scanner, or coupled to a bed of the MRI scanner. Presence of metal in the subject may be detected based on a distinct signature of wave reflection from metals, thereby allowing presence and location of the implant to be revealed. Reflection of ultrasound waves may also allow evaluation of tissue surrounding the implant. Ultrasound may be used in combination with a pre-screen modality for creating a 3-D body model of the subject.

The controller unit assesses tissue healing at 720 when either infrared thermography is performed at 716 and/or ultrasound detection executed at 718. If the tissue surrounding the implant does not reach or exceed a threshold, e.g., minimum, amount of healing, an alert may be displayed at a user interface of the MRI scanner at 722. The threshold amount of healing may be based on a thermal signature of tissue surrounding the implant, for example, and comparing the thermal signature of the tissue to thermal patterns generated by tissue removed, e.g., at a distance, from the implant. The threshold amount of healing may be a minimum difference between a thermal pattern of the tissue surrounding the implant versus a thermal pattern of tissue at a distance from the implant. Generation of the alert may inhibit activation of the MRI scanner so that an operator may not command operation of the MRI scanner. The method ends.

If the tissue surrounding the implant is determined to be healed to an extent at least equal to the threshold amount, confirmation of presence of the implant is obtained at 724. If no implant is found, affirmation that an MRI procedure may proceed is displayed on a user interface of the MRI scanner at 726. The controller unit may command display of a message on the user interface indicating that MRI may be performed. The method ends. If the implant is detected, it is determined whether the implant is ferromagnetic at 728. If the implant is ferromagnetic, an alert is displayed on a user interface of the MRI scanner at 730. Generation of the alert may inhibit activation of the MRI scanner so that an operator may not command operation of the MRI scanner. The method ends.

If the implant is not ferromagnetic, the 3-D image, or body model, of the subject is displayed at the user interface at 732. The body model reflects a height and size of the subject. The detected implant is also displayed at 732, shown in a position in the body model that represents an actual location of the implant in the subject. The implant is identified by analysis with an implant database at 734. Information regarding the implant may be manually entered by an operator or the controller unit may be configured to match the implant through a registration system to known types of implants, based on location and implant shape. Alternatively or additionally, the controller unit may be configured to identify the implant via machine learning in a system adapted with a deep neural network.

In instances where the implant is not matched to an implant in the implant database, a nominal set of MRI operating parameters may be used. The nominal operating parameters may be pertaining to a conservative MRI approach based on the unidentified implant.

Guidelines and alerts for the MRI procedure are displayed on the user interface at 736. The guidelines and alerts may include recommendations for additional preparation of the subject and/or implant at 738 such as adjusting a mode of the implant to a suitable mode for MRI, and/or removing the implant if removable.

The guidelines and alerts may also include suggestions for localized energization of RF coils or use of particular landmarks specific to the type of implant at 740 based on identification through the implant database. Instructions for positioning the subject to enable location of the implant within the below-threshold zone of the spatial gradient may be shown at 742. The method ends.

The technical effect of implementing a pre-screen procedure prior to MRI is that efficient and accurate detection of an implant may be rapidly achieved and identified based on an implant database for any MRI subject. Further, mensurable and comprehensive guidance for maintaining the implant at below-threshold magnetic field strength may be provided according to information acquired through the pre-screen procedure.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a pre-screen procedure for magnetic resonance imaging (MRI), comprising:
   using an imaging scanner of a pre-screen system to obtain data comprising a body model of a subject and a presence of an implant in the subject, the pre-screen system arranged in a remote location relative to an MRI system and communicatively coupled to the MRI system, wherein using the imaging scanner of the pre-screen system to obtain data comprising the presence of the implant includes, via the imaging scanner of the pre-screen system scanning the subject's body:
   detecting that the implant is present in the subject, determining a location and a shape of the implant, and determining that the implant is not ferromagnetic;
   sending the data comprising the body model of the subject and the presence of the implant in the subject from the pre-screen system to a controller unit of the MRI system;
   in response to determining that the implant is not ferromagnetic;
   overlaying the implant onto the body model of the subject at a location on the body model that represents an actual location of the implant in the subject, and displaying the implant overlaid onto the body model at a display device of the controller unit;
   identifying a type of the implant, wherein identifying the type of implant comprises matching the implant to an implant database, wherein matching the implant to the implant database is based on the location of the implant and the shape of the implant, and comprises comparing a geometry of the implant, as determined by the imaging scanner of the pre-screen system, to three-dimensional shapes of implants in the implant database;
   displaying an identification of the type of the implant at the display device; and
   displaying guidelines for an MRI procedure at the display device in response to the identification of the type of the implant.

2. The method of claim 1, wherein the body model is a three-dimensional body model.

3. The method of claim 1, further comprising, using the pre-screen system to obtain data comprising a body model of another subject having an implant that is ferromagnetic, and in response to determining that the implant detected in the another patient is ferromagnetic, displaying an alert to an operator and inhibiting activation of an MRI scanner of the MRI system so that the operator is prevented from commanding operation of the MRI scanner.

4. The method of claim 1, wherein the guidelines include at least one of suggesting adjusting a mode of the implant to an MRI compatible mode, recommending removal of the implant when the implant is configured to be removable, and suggesting landmarks and coil energization.

5. The method of claim 1, further comprising determining a value of table movement speed based on the identification of the type of the implant, the location of the implant determined by the pre-screen system, the body model generated by the pre-screen system, and a spatial gradient of a magnetic resonance scanner, and displaying the value of table movement speed at the display device.

6. The method of claim 1, wherein the imaging scanner of the pre-screen system comprises both a terahertz (THz) device and an electromagnetic induction device, wherein using the imaging scanner of the pre-screen system to obtain data comprises using the THz device to obtain the body model of the subject and using the electromagnetic induction device to detect the presence of the implant, wherein overlaying the implant onto the body model comprises overlaying the implant detected by the electromagnetic induction device onto the body model generated by the THz device via an image registration process; and wherein the imaging scanner is a full-body scanner located in a remote location relative to both the MRI system and the controller unit of the MRI system.

7. The method of claim 1, wherein the imaging scanner of the pre-screen system comprises one or more of a THz device, an electromagnetic induction device, a Kinect 3-D sensor, an array of Hall sensors, an infrared thermography device, and an ultrasound device, and wherein the imaging scanner of the pre-screen system further comprises a camera configured to capture live images of the subject while a processor of the pre-screen system determines a position of the subject based on the live images.

8. A magnetic resonance imaging system comprising:
   an MRI scanner positioned in a scan room;
   a display device;
   a controller unit communicatively coupled to the MRI scanner and the display device;
   a pre-screen system communicatively coupled to the controller unit and arranged in a location remote relative to both the MRI scanner and the controller unit, the pre-screen system comprising a scanner, wherein the scanner is an imager and comprises:
   a first imaging modality configured to generate a body model of a subject positioned within the scanner, and a second imaging modality configured to identify a presence of an implant in the subject positioned within the scanner; and a memory storing executable instructions that, when executed, cause the controller unit to:

receive data from the scanner of the pre-screen system, wherein the data comprises the body model of the subject and the presence of the implant in the subject, wherein data comprising the presence of the implant includes whether the implant is present in the subject and, if the implant is present in the subject, whether the implant is ferromagnetic, wherein data of whether the implant is present in the subject is determined by scanning a body of the subject via the scanner to determine if the implant is present inside the body of the subject;

if the implant is not ferromagnetic, identify an implant type based on a matching of the implant to an implant database;

instruct the display device to display the implant relative to the body model; and if the implant is not ferromagnetic, instruct the MRI scanner to scan the subject based on the identification of the implant type.

9. The magnetic resonance imaging system of claim 8, wherein the pre-screen system comprises a THz device as the first imaging modality to obtain the body model and an electromagnetic induction device as the second imaging modality to provide data for the presence of the implant.

10. The magnetic resonance imaging system of claim 8, wherein the pre-screen system comprises one or more of a Kinect 3-D sensor, an array of Hall sensors, an infrared thermography device, and an ultrasound device, and wherein the pre-screen system further comprises a camera configured to capture live images of the subject while a processor of the pre-screen system determines a position of the subject based on the live images.

11. The magnetic resonance imaging system of claim 8, wherein the pre-screen system comprises at least one of an infrared thermography device or an ultrasound imaging device configured to assess an extent of tissue healing surrounding an implant via one of infrared thermography and ultrasound imaging, wherein the pre-screen system comprises executable instructions that, responsive to the extent of tissue healing being below a threshold, cause the controller unit to generate an alert at the display device, wherein generating the alert at the display device inhibits activation of the MRI scanner.

12. The magnetic resonance imaging system of claim 8, wherein the body model is a three-dimensional body model, wherein the implant is displayed via the display device relative to the body model by overlaying the implant on the body model at a location where the implant is located via an image registration process, and wherein alerts corresponding to the implant are further displayed via the display, the alerts relaying data about the implant type from the implant database.

13. The magnetic resonance imaging system of claim 8, wherein the pre-screen system comprises executable instructions that cause the controller unit to:

display an alert for terminating the MRI in response to the implant being detected to be ferromagnetic; and display guidelines based on the identification of the implant type, wherein the guidelines include at least one of suggesting adjusting a mode of the implant to an MRI compatible mode, recommending removal of the implant when the implant is configured to be removable, and suggesting landmarks and coil energization.

14. The magnetic resonance imaging system of claim 8, wherein the matching of the implant to the implant database is based on a three-dimensional shape and a location of the implant as determined by the pre-screen system.

15. The magnetic resonance imaging system of claim 8, wherein a value of table movement speed is displayed and wherein the value of table movement speed is determined based on the identification of the implant type and spatial gradient of a magnetic resonance scanner.

16. A method comprising:

scanning, by a scanner of a pre-screen system, a body of a subject to obtain a body model of the subject and to detect a presence of an implant wherein the scanner is an imager, wherein scanning by the pre-screen system to detect the presence of the implant includes detecting that the implant is present in the body of the subject and determining that the implant is not ferromagnetic, wherein the scanner uses one or more of infrared thermography, ultrasound, terahertz (THz) scanning, and electromagnetic induction;

identifying, by a processing system, a type of implant, wherein identifying the type of implant comprises matching the implant to an implant database based on a location of the implant and a shape of the implant, wherein matching the implant to the implant database based on the shape of the implant comprises comparing a geometry of the implant, as determined by the scanner of the pre-screen system, to three-dimensional shapes of implants in the implant database;

displaying, by a display device, the implant relative to the body model; and performing, by an MRI system, an MRI scan according to the identified type of the implant;

wherein data comprising the body model of the subject and the presence of the implant in the subject is sent by the pre-screen system to the MRI system.

17. The method of claim 16, wherein the scanner comprises a THz device in order for the scanner to use the THz scanning, and wherein scanning the subject comprises:

scanning the subject with the THz device to obtain the body model; and scanning the subject with an electromagnetic induction device to detect the presence of the implant.

18. The method of claim 17, wherein displaying the implant relative to the body model comprises overlaying the implant detected by the electromagnetic induction device onto the body model obtained by the THz device at a position in the body model that represents an actual location of the implant in the subject via an image registration process.

19. The method of claim 16, wherein performing the MRI scan according to the identified type of the implant comprises adjusting one or more parameters for the MRI scan.

20. The method of claim 19, wherein the one or more parameters comprise a speed of moving the subject in and out of the MRI system.

\* \* \* \* \*